United States Patent [19]

Hsu et al.

[11] Patent Number: 4,961,252
[45] Date of Patent: Oct. 9, 1990

[54] MEANS AND METHOD FOR NONUNIFORM POLING OF PIEZOELECTRIC TRANSDUCERS

[75] Inventors: David K. Hsu; Frank J. Margetan; Michael D. Hasselbusch; Samuel J. Wormley; Michael S. Hughes; Donald O. Thompson, all of Ames, Iowa

[73] Assignee: Iowa State University Research Foundation, Inc., Ames, Iowa

[21] Appl. No.: 447,831

[22] Filed: Dec. 8, 1989

[51] Int. Cl.$^5$ .......................................... H01L 41/22
[52] U.S. Cl. .................................. 29/25.35; 264/22; 310/359; 310/369
[58] Field of Search .............. 29/25.35; 310/357–359, 310/369; 264/22

[56] References Cited

U.S. PATENT DOCUMENTS

| | | |
|---|---|---|
| 1,896,513 | 2/1933 | Hovgaard . |
| 2,420,864 | 5/1947 | Chilowsky ........................ 171/327 |
| 2,708,244 | 5/1955 | Jaffe ................................. 310/8 |
| 2,875,355 | 2/1959 | Petermann ........................ 310/9.5 |
| 2,928,068 | 3/1960 | Samsel et al. .................... 340/10 |
| 3,430,316 | 3/1969 | Schafft ............................. 29/25.35 |
| 3,766,615 | 10/1973 | Shimizu ............................ 29/25.35 |
| 4,412,148 | 10/1983 | Klicker et al. ................... 310/358 |
| 4,460,841 | 7/1984 | Smith et al. ...................... 310/334 |
| 4,518,889 | 5/1985 | 'T Hoen ........................... 310/357 |

Primary Examiner—Carl E. Hall
Attorney, Agent, or Firm—Zarley, McKee, Thomte, Voorhees & Sease

[57] ABSTRACT

An apparatus and method for nonuniform poling of piezoelectric transducers includes machining one or more indentation into an end of a piezoelectric rod and cutting the rod to present a thickened disk shape. Highly electrically conductive material is deposited on at least the indentations in the one end and on at least portions of the opposite face of the member. One or more electrodes are configured to matingly fit within the indentations on the one face of the disk, with a like number of electrodes being positionable on the opposite face of the material. Electrical power is then applied to the electrodes in desired amounts, polarity, and duration. The indentations vary the electrical field produced within the piezoelectric material to produce nonuniform poling in the material. The thick disk is then cut to remove the indentations and to present a thin, flat two sided disk for installation in a conventional piezoelectric transducer probe. The indentations are selected to produce poling in accordance with desired transducer response profiles such as Gaussian or Bessel functions.

33 Claims, 7 Drawing Sheets

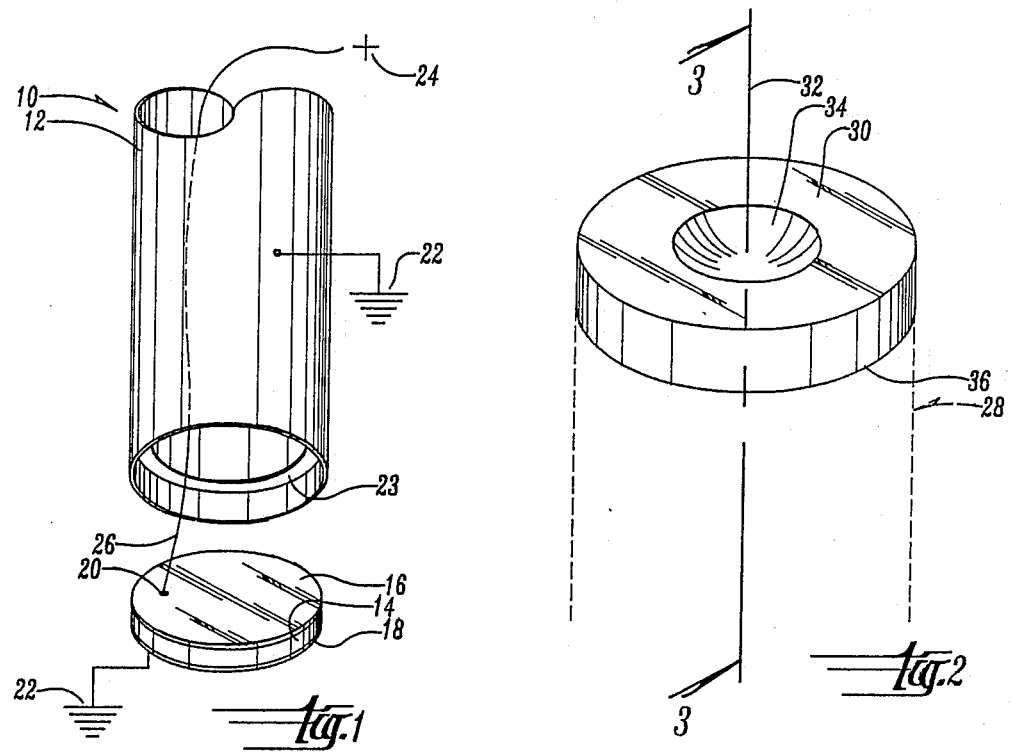
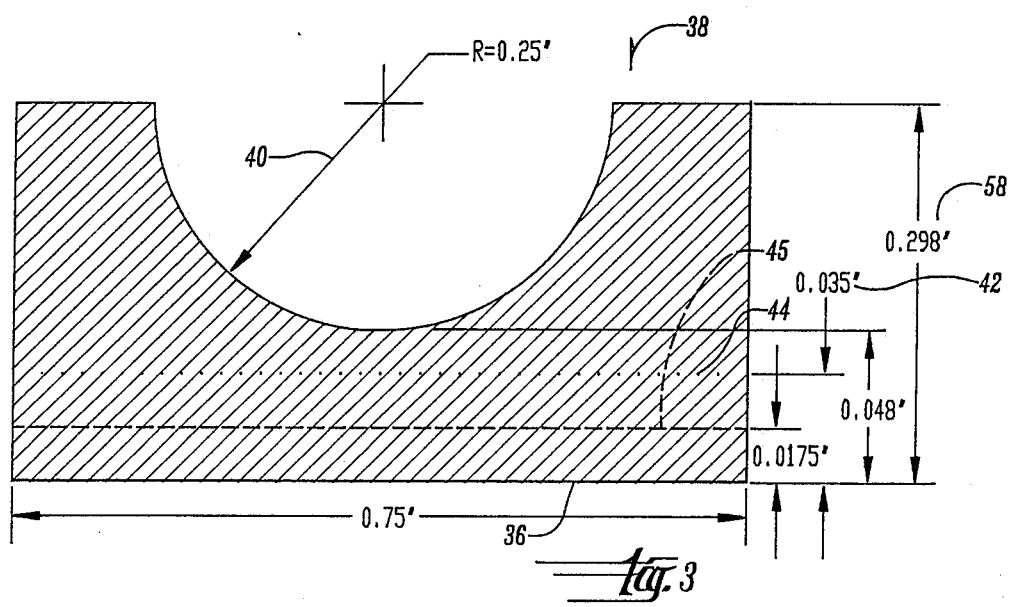

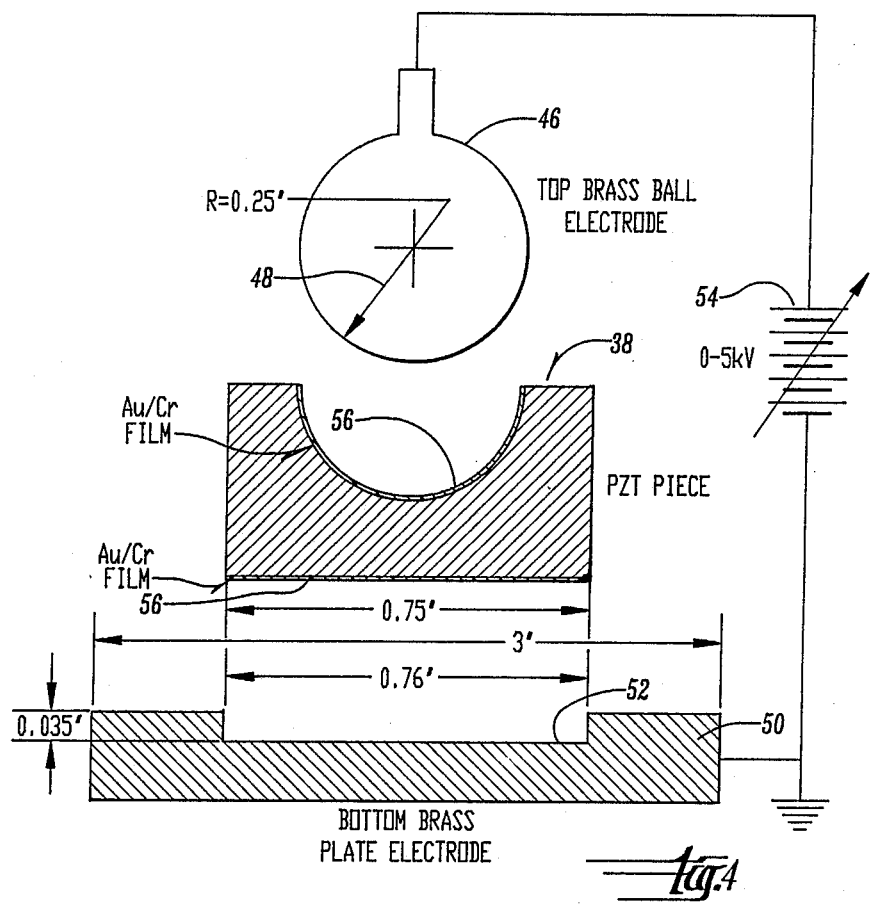
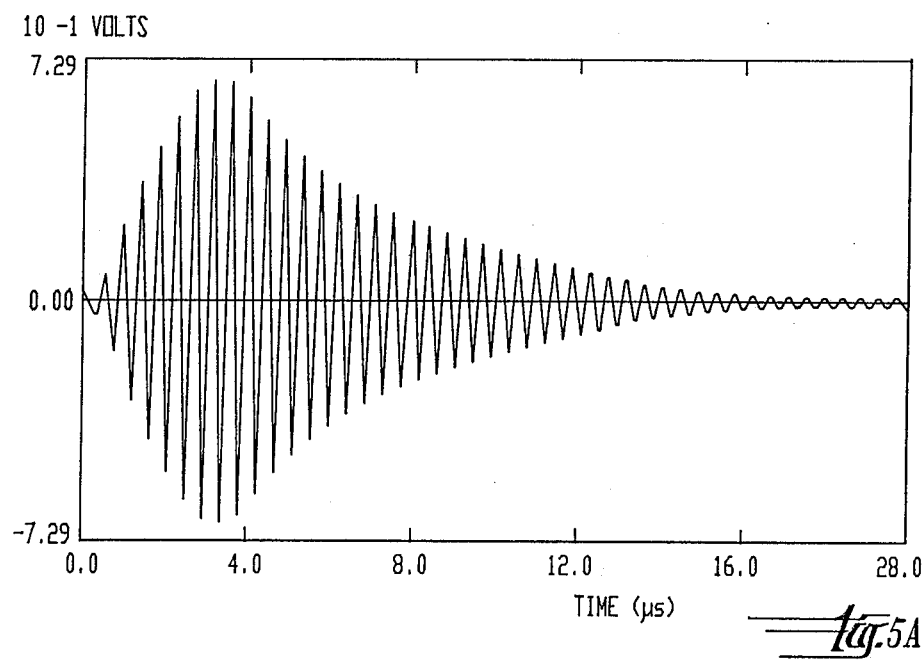

MEANS AND METHOD FOR NONUNIFORM POLING OF PIEZOELECTRIC TRANSDUCERS

GOVERNMENT RIGHTS

This invention was made with Government support under Contract No. W-7405-ENG-82 awarded by the Department of Energy. The Government has certain rights in this invention.

BACKGROUND OF THE INVENTION

A. Field of the Invention

This invention relates to piezoelectric transducers, and more particularly, to a means and method for nonuniform poling of piezoelectric transducers.

B. Problems in the Art

Piezoelectric transducers are utilized for a wide variety of applications. A few examples are ultrasonic holography, acoustic imaging, and nondestructive evaluation using electromagnetic transduction such as ultrasound. These uses and advantages of piezoelectric transducers are well known in the art.

A piezoelectric transducer used, for example, with nondestructive evaluation ultrasonic inspection, generally consists of a disk of piezoelectric ceramic material (an example of which is referred to as PZT) connected to electrical leads and mounted in a housing. The disk is prepared for use by poling, that is, setting the polarization throughout the disk. This means that electrical energy is passed through the disk for a period of time. The disk is then installed within the transducer case or housing and is electrically connected to circuitry.

Operation of piezoelectric ultrasonic transducers is well known in the art. To transmit ultrasonic energy, a timedependent electrical voltage is supplied to the piezoelectric disk. This causes the disk to vibrate, which in turn produces high frequency sound waves.

The transducer can also serve as a receiver. The piezoelectric disk would receive sound energy, vibrate in kind, and in turn produce a small electrical signal proportional to received sound energy. This signal can be amplified for further use.

The process of poling of the disk, that is, producing an initial polarization in the disk before utilizing the disk in the transducer, is critical to how the transducer operates. Normally, the disk is uniformly poled. What this means is that a uniform electrical field is applied across the disk by attaching electrodes on opposite sides of the disk. A conductive layer is spread across both sides of the disks so that the electrical potential proposedly spreads out evenly through the disk.

The way the piezoelectric element is poled determines its response pattern or profile. This is important in achieving reliable and interpretable results using such transducer.

For example, use of these types of transducers in ultrasonic nondestructive evaluation requires that the ultrasonic beam pattern be generally known both so that the results obtained by monitoring the reflection of the ultrasonic energy can be accurately and reliably determined; and also to allow the ultrasonic energy to have a beam profile or pattern which is as effective as possible in analyzing materials for flaws (e.g. eliminate disadvantageous beam characteristics such as near field oscillations or side lobes; reduce or eliminate diffraction of the beam; or create a beam whose reflections can be more accurately analyzed). Conventional uniformly poled piezoelectric transducers produce an approximately uniform field across their face. While they may be easy to fabricate, the field patterns produced by uniformly poled transducers are complicated.

For example, the field patterns of uniformly poled piezoelectric transducers have large amplitude oscillations in the near field. There are also side lobes in the beam profile. Even though these types of patterns are well known in the art, they produce complexities and disadvantages in such applications as nondestructive evaluation.

Examples of these problems are as follows. The large oscillations in the near field on-axis pressure contain nulls. Flaws located at the near field nulls can therefore easily escape detection. Secondly, in quantitative nondestructive evaluation, the complicated beam profile from uniformly poled transducers requires complicated analytical techniques. As a practical matter, these complications are significant enough to result in substantially more processing time and steps than if a simpler or different beam pattern was available.

It is important to understand that the disadvantage of the complicated analysis required for uniformly poled transducer beams is substantial and significant. To derive relevant and meaningful information from ultrasonic evaluation, tremendous amounts of computing and processing time are needed. This requires dedication of a certain significant amount of computing power, and of course, requires substantial time. Any reduction in these requirements is beneficial. Elimination of detrimental beam profiles shapes and utilization of advantageous beam profile shapes can result in substantial, if not staggering reductions in processing computation time. In some cases, this reduction can be as great or greater than 1,000 fold.

Another example of a problem in the art is that conventional ultrasonic beams from uniformly poled transducers, like most energy beams, experience significant diffraction or beam spreading over distance. Thus, the effective range of such beams is limited. Diffraction must also be taken into consideration in analyzing the beam or any reflections of the beam for purposes of such things as ultrasonic testing or ultrasonic nondestructive evaluation.

If diffraction of ultrasonic beams could be reduced or eliminated, effective range of the beam would be significantly improved, and many additional uses for ultrasonic evaluation would be enhanced. New applications might also be developed. It has been reported that by altering the beam profile of electromagnetic waves into a form defined by a Bessel function, diffraction of the beam can be significantly reduced or eliminated. If similar beam-shaping could be applied to ultrasound transducers, it may be possible to eliminate diffraction problems with acoustic waves. Uniformly poled transducers exhibit these diffraction problems.

It can therefore be seen how a uniformly poled transducer can be deficient in certain applications. A need exists, therefore, for transducers which did not exhibit the problems and deficiencies of a uniformly poled transducer.

It has been determined that if the transducer could be made to vibrate in such a way that the amplitude profile at the face of the transducer followed a Gaussian function, being a maximum at the center and falling off like a Gaussian function toward the perimeter, the beam profile would be extremely simple, which would solve the above mentioned problems. The Gaussian shaped beam would not have oscillations in its axial amplitude and would not have side lobes. Furthermore, the transverse profile of a Gaussian beam is described by a Gaussian function at any distance from the transducer.

As is well known in the art, a Gaussian function is approximately a bell-shaped curve when graphed. Attempts have then been made to produce such a piezoelectric transducer so that it generates what would be called a Gaussian beam.

Most of these attempts involve utilizing a uniformly poled piezoelectric transducer disk, but operating the disk by a nonuniform driving voltage and field. In other words, preparation and initial poling of the disk would be by conventional methods resulting in a uniformly poled disk. However, the electrical voltage utilized to drive the transducer would be presented to the uniformly poled disk in a nonuniform way; and particularly, approximating that of a Gaussian.

One such method utilized an eight-pointed star-shaped electrode on one face of the uniformly poled transducer disk or element. The driving voltage and field presented through that star-shaped electrode approximated a Gaussian function. This method is described in K. V. Haselberg and J. Krautkramer, "Ein Ultraschall-Strahler fur die Werkstoffprufung mit Verbessertem Nahfeld", Acustica 9, 359–364 (1959).

Others produced approximate Gaussian beams by utilizing a full electrode plating on one face of the uniformly poled transducer element, but used a small electrode with a diameter equal to about three times the thickness on the other face. See F. D. Martin and M. A. Breazeale, "A Simple Way to Eliminate Diffraction Lobes Emitted by Ultrasonic Transducers", J. Acoust. Soc. Am. 49, 1668–1669 (1971) and G. Du and M. A. Breazeale, "Ultrasonic Field of a Gaussian Transducer", J. Acoust. Soc. Am. 78, 2083–2086 (1985). Other attempts utilized electrodes positioned on the uniformly poled disk made of concentric rings each driven by a different voltage provided by a voltage divider network. See P. S. Zerwekh and R. O. Claus, "Ultrasonic Transducer with Gaussian Radial Velocity Distribution", in Proc. 1981 IEEE Ultrason. Symp., Cat. No. 81CH1689-9; and R. 0. Claus and P. S. Zerwekh, "Ultrasonic Transducer with a Two-Dimensional Gaussian Field Profile", IEEE Trans. Sonics and Ultrasonics, 30, 36–39 (1983).

These methods did produce approximate Gaussian transducer response profiles to eliminate near field oscillations and diffraction side lobes. However, all of these methods require the additional structure and complexity of means and methods to provide nonuniform driving voltages and fields to a uniformly poled transducer element.

A more recent attempt to provide a Gaussian function piezoelectric transducer can be found at U.S. Pat. No. 4,518,889 to T Hoen. In this approach, a matrix of parallel rods of piezoelectric ceramic is configured to operate as the transducer element. Different polarizations to different regions of that composite element are then produced. The T Hoen patent also briefly alleges that the flat non-uniformly poled piezoelectric element can be produced by abutting a block of material to one of the element faces. The block of material has electrical properties such as resistivity and dielectric constant which effectively form a voltage divider. Electricity is then passed through the block of material and the flat element. This patent then alleges (without giving evidence) the polarization of the flat PZT element will be nonuniform, and can be Gaussian, based on the geometry and configuration of the block of material.

The T Hoen patent therefore also has a similar deficiency of requiring rather complex structure to produce a nonuniform poled transducer element. The parallel rods do not make a continuous transducer surface. Additionally, the above-described alternative method utilizing the block of material is not believed to be functional. The high dielectric constant of piezoelectric ceramic makes it impossible to polarize the piezoelectric element because almost all the voltage will be dropped across the gap between such a block of material and the piezoelectric disk.

It can therefore be seen that there is a real need in the art for a nonuniformly poled piezoelectric transducer. Not only is there a need to be able to create transducers which do not exhibit the deficiencies of uniformly poled transducers, but there is also a need to be able to selectively incorporate nonuniform poling of a variety of different beam profiles for various applications. Still further, there is a need to be able to produce nonuniformly poled transducers which do not require complex driving voltages or apparatus to provide nonuniform driving voltages, or specially configured composite transducer elements. There is a real need to have a nonuniformly poled transducer which can be incorporated into standard conventional transducer probes.

It is therefore a primary object of the present invention to provide a means and method for nonuniform poling of piezoelectric transducers which solves or improves over the problems and deficiencies in the art.

A further object of the present invention is to provide a means and method as above described which allows different poling or field profiles to be introduced into piezoelectric transducer elements.

A further object of the present invention is to provide a means and method as above described which allows specific functions such as Gaussian or Bessel functions to be incorporated into the response and beam profiles of transducer elements.

Another object of the present invention is to provide a means and method as above described which allows elimination of the near field nulls and side lobes in the response patterns, if desired, of uniformly poled transducers.

Another object of the present invention is to provide a means and method as above described which allows creation of response and beam profiles of desired mathematical functions.

A still further object of the present invention is to provide a means and method as above described which minimizes diffraction or beam spreading of the beam, if desired, to reduce beam spreading which would diminish dissipation of the beam or distance it can penetrate.

Another object of the present invention is to provide a means and method as above described which allows generation of specific beam patterns such as Bessel function or Gaussian function patterns.

Another object of the present invention is to provide a means and method as above described wherein the transducer has a large range if desired.

A further object of the present invention is to provide a means and method as above described which allows beam width and frequency to be varied independently, if desired.

A further object of the present invention is to provide a means and method as above described which allows production of a nonuniformly poled piezoelectric transducer which is of the same physical structure and dimensions as a conventional uniformly poled element so that it can be directly incorporated into existing transducer probes without modification.

Another object of the present invention is to provide a means and method as above described which is efficient, economical, and reliable.

These and other objects, features, and advantages of the present invention will become more apparent with reference to the accompanying specification and claims.

SUMMARY OF THE INVENTION

The present invention consists of a means and method for nonuniform poling of piezoelectric transducers. The means and method ultimately produce a piezoelectric transducer disk which has the basic identical physical dimensions and characteristics as a conventional uniformly poled disk, which generally can be described as a parallel plate capacitor configuration. This allows the transducer elements according to the present invention to be packaged, backed (if desired), and electroded in the same way as conventional transducers. The nonuniform poling of such a disk allows it to produce field or beam profiles of desired characteristics without requiring additional complex structure or complex driving voltages.

The invention presents a non-complex and efficient way to produce the nonuniformly poled transducer disks, which will hereafter sometimes be referred to as transducer disks. Different parts of the disk are poled to different strengths. Predetermined spatial patterns of the polarization strength can be built into the transducer disk to achieve desired field profiles from the disk.

A piece of piezoelectric ceramic material of a thickness greater than the thickness of what ultimately will be the transducer disk initially is presented with generally parallel flat opposite faces. One face is left flat. The other face is altered by machining or other processes to create indentations in the surface according to the type of transducer response ultimately desired.

For example, to produce a Gaussian beam pattern, a hemispherical cavity would be machined in the center of the surface. If a 3—lobe Bessel function is desired, a hemispherical cavity would be machined in the center, along with two concentric hemispherical channels around the center hemispherical indentation. It is to be understood that other response patterns can be produced by different alterations to the piezoelectric material.

Upper and lower electrodes are then brought into position with respect to the upper and lower surfaces of the piezoelectric material. To ensure electrical conduction through the piezoelectric material, a highly electrical conducting layer, such as a metal film, can be, for example, evaporated onto both surfaces of the piezoelectric material. The metalization (evaporation of metal film onto piezoelectric ceramic surfaces) must be done in a manner to specifically cover certain flat and/or curved piezoelectric ceramic surface areas in order to generate the desired poling fields (e.g. Gaussian or Bessel) in the disk.

The electrodes are then brought into contact and according to the desired ultimate beam profile, electric voltage of predetermined magnitude, polarity, and duration is applied through the piezoelectric material. In some cases, multiple electrodes are positioned on opposite sides with varying polarities of voltage being applied on each side.

Polarization of the piezoelectric material and thus the ultimate beam pattern depend on the number of parameters including, but not limited to, thickness of the piezoelectric material, magnitude of voltage, shape of the indentations or alterations made in the surface of the material, duration of application of the voltage, and temperature.

After the poling electrodes are removed from the piezoelectric material, the piezoelectric material is cut to remove the indentations and to produce a piezoelectric disk of desired thickness. The thickness is directly related to the center frequency of the beam which will ultimately be produced by the disk. Both upper and lower surfaces of the disks are then coated (e.g. by metallization or evaporation) with a metal film across required surfaces, if not already in place, and the piezoelectric disk is then ready to be mounted in a conventional transducer probe housing or case. Appropriate electrical connections are then made and the transducer is ready for operation to produce a beam response pattern of desired shape from the nonuniformly poled disk Different beam profiles are obtained by different machining or alteration of one surface of the piezoelectric material and then the pre-selected application of electrical voltage to the piezoelectric material. The final piezoelectric disk consists solely of a flat parallel circular piezoelectric disk covered on both sides with electrically conducting material such as an evaporated metal film. The disk may or may not be backed according to need or desire. There is no requirement of specialized equipment, additional components, or specialized methods for driving the disk once installed in the transducer probe. The invention therefore represents an efficient, economical way to produce conventionally shaped piezoelectric transducer disks for use in current, conventional transducer probes, but where the disks exhibit desired beam profile shapes different from uniformly poled transducer disks.

BRIEF DESCRIPTION OF THE DRAWINGS

FIG. 1 is a perspective view of a transducer probe.

FIG. 2 is a perspective view of piezoelectric piece with a hemispherical cavity machined into one end.

FIG. 3 is an enlarged sectional elevational view taken along lines 3—3 of FIG. 2.

FIG. 4 is a sectional elevational view and schematic of the configuration for poling the piezoelectric piece of FIGS. 1 and 2.

FIG. 5(a) is a graph of the response pattern of a piezoelectric transducer disk produced according to steps shown in FIGS. 2–4, graphing the response as a function of time.

DETAILED DESCRIPTION OF THE PREFERRED EMBODIMENTS OF THE INVENTION

Figure 5B:
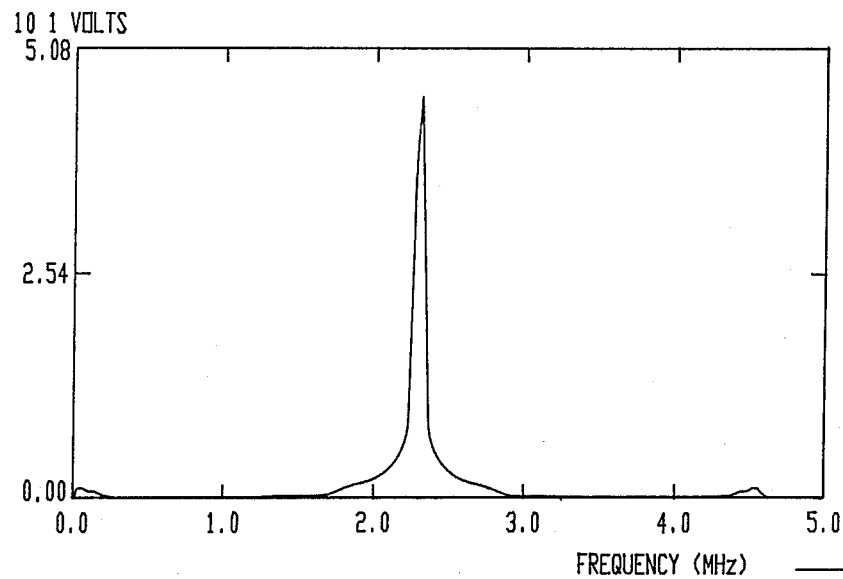
FIG. 5(b) is a graph of the response pattern of the piezoelectric transducer disk of FIGS. 2–4, graphing response as a function of frequency.

A detailed description of preferred embodiments of the invention will now be set forth. This description is to aid in an understanding of the invention, but does not limit the invention to these embodiments. Reference in this description will be taken to the drawings. Reference numerals are utilized to denote specific elements or features in the drawings. Like reference numerals will be utilized throughout this description unless otherwise noted.

Two embodiments of the invention will be described. The first embodiment represents a means and method for producing a piezoelectric transducer having what will be sometimes called a Gaussian beam response. The second embodiment produces a non-uniformly poled piezoelectric transducer with what will be called a Bessel beam response. It is to be understood that the invention is not limited to Gaussian or Bessel beam responses and that methods of poling transducers to generate beam patterns of different natures are contemplated while staying within the boundaries of the invention; just as other types of beam responses can be created with the invention. This detailed description of the two embodiments will give the reader an understanding of how the invention is utilized with respect to Gaussian and Bessel beam response patterns. Similar procedures can be used to create non-uniformly poled piezo-electric transducers with other types of response patterns.

With particular reference to FIG. 1, a transducer probe 10 is shown in simplified exploded perspective form. The probe 10 includes a conventional piston probe tubular housing or case 12 into which a round piezoelectric disk 14 can be mounted. Disk 14 has conductive surfaces (usually metal films) 16 and 18 bonded or deposited to opposite sides, and a connection tab 20 attached to surface 16.

In this embodiment of probe 10, case 12 is made of metal and is configured so that it conductively contacts surface 18 when disk 14 is inserted into case 12. Case 12 is electrically grounded at ground 22. Disk 14 could, for example, be inserted from the top of case 12 and rest on metal annular interior flange 23, so that surface 18 is grounded. Other configurations to connect surface 18 to ground when disk 14 is mounted in case 12 could be utilized. It is to be understood that FIG. 1 shows an unbacked transducer, and that Gaussian, Bessel, or any transducers of this invention can be backed if desired, as is known within the art.

An excitation electrical voltage from electrical source 24 is communicated by wire 26 to surface 16 via connection tab 20.

Probe 10 depicts the general configuration for a conventional piezoelectric transducer probe. Such a configuration is well known within the art. By application of electrical power to disk 14, the piezoelectric material of disk 14 vibrates in response to the electricity in such a fashion to produce high frequency ultrasonic waves.

The physicial characteristics of the disk 14 (e.g. diameter, thickness, etc.), as well as the spatial pattern of polarization strength along the disk 14, are factors which affect the beam pattern of the ultrasound transmitted by the transducer probe 10.

A primary feature of the present invention is that piezoelectric transducer disks such as disk 14 can be produced which have nonuniform polarization across their faces, and that this can be accomplished by preparation of the flat circular disk so that it can be inserted into a conventional probe such as probe 10 without any modifications or retrofitting. The invention therefore provides the desired objective of nonuniform poling and specified, selected probe response patterns, without complex and expensive additional components or operation.

The benefits of a Gaussian transducer response pattern, as compared to a uniform probe response pattern have been previously discussed. By referring to FIGS. 2–7, the method and apparatus for producing Gaussian piezoelectric transducer disks, in the physical form of disk 14 of FIG. 1, will be described. FIG. 2 shows an end portion of a piezoelectric ceramic rod 28 (in this embodiment 0.75 inches in diameter) having a flat end surface 30 perpendicular to the longitudinal axis 32 of rod 28.

A hemispherical cavity is machined into the center of end surface 30, centered around axis 32. This can be accomplished by using a ball cutter available from L. R. Oliver and Co., Inc., Anchorville, Mich. 48004, or by other means. In the preferred embodiment, a ball cutter is utilized covered with surface abrasive particles. The ball cutter is spun at high speed at an angle relative to axis 32 to avoid the zero velocity point at the tip of such a ball cutter. It is advanced slowly into rod 28 utilizing water as a lubricant for cutting. The ball cutter is rotated slowly at the end of the process to achieve a smooth finish for hemispherical cavity 34.

The end of rod 28 is then cut off along line 36 to produce a piece 38 such as is shown in enlarged cross section in FIG. 3. A thickness between line 36 and line 44 beneath the bottom of the hemispherical cavity 34 is preserved which will ultimately define the flat two sided disk 14 used in transducer probe 10.

It is to be understood that a variety of parameters determine the ultimate poling of disk 14 produced by this method. Some of these parameters are radius 40 of hemispherical cavity 34; thickness 42 of the final disk 14 cut from piece 38 (the distance between line 36 and line 44); magnitude of voltage applied during poling; length of time of voltage application during poling; and the poling temperature. These parameters are therefore selected according to preselected criteria to produce piece 38 as shown in FIG. 3.

FIG. 4 depicts the apparatus for poling piece 38. A top electrode 46, in the configuration of a brass ball with a radius 48 similar to that of hemispherical cavity 34 is adapted to be positioned into hemispherical cavity 34. A bottom brass electrode 50 having a circular, flat-bottomed indentation 52 of similar diameter to the diameter of the bottom of piece 38 is adapted to receive the bottom of piece 38.

As is shown in FIG. 4, electrode 46 is connected to the positive side of a variable electrical power source 54, whereas bottom electrode 50 is connected to the negative and ground side of power source 54.

Piezoelectric material such as piece 38 has an extremely high dielectric constant. If electrodes 46 and 50 were abutted directly against piece 38, this high dielectric constant would cause almost all of the applied poling voltage to drop across the gap or gaps at the abuttments, instead of through the piezoelectric material to polarize the material. A thin layer or film of highly conductive material is therefore bonded to hemispherical cavity 34 and to the bottom surface 56 of piezoelectric piece 38. In the preferred embodiment, this is a gold-over-chromium film. The chromium layer is deposited first for good adhesion to the piezoelectric ceramic. It is to be understood that other conducting layers and materials can be used.

The electrodes 46 and 50 are then brought into mating contact with piece 38 (with conducting layers therebetween) and power source 54 is operated to apply a high DC voltage across piece 38. It is to be understood that the gold plating of hemispherical cavity 34 allows the top ball of electrode 46 to not necessarily precisely match the size and shape of hemispherical cavity 34 as long as electrode 46 makes good electrical conduct with the plating in the cavity. Additionally, it is to be understood that bottom surface 56 of piece 38 is recessed into indentation 52 in electrode 50 so that the vertical component of the electrical field is forced to zero at the lower corners. It is believed that this creates an electrical field through the piece 38 closer to a Gaussian field than without indentation 52.

It is to be understood that the electrodes 46 and 50 are held in position by a fixture made of highly insulating material, such as a cage made of plexiglas (not shown). Other types of fixtures are of course possible.

The electrical field is employed through piece 38 for a selected duration while the electrodes and the piezoelectric material are held at an elevated temperature (about 95° ±2° C.). Piece 38 is then removed and the portion of piece 38 containing hemispherical cavity 34 is cut away above line 44 in FIG. 3 to produce piezoelectric transducer disk 14 (see FIG. 1).

For use in transducer 10, both faces of disk 14 are plated with conductive material. In this embodiment, the bottom surface is already coated with the gold and chromium film. The top exposed face (along cut line 44) is then also coated with the same plating. Disk 14 is then mounted within metal case 12. The bottom face, coated with surface 18, is shorted to metal case 12, and small metal tab 20 is attached to the top face near the outer rim for connection to wire 26 to the electrical power source 24. Tab 20 is located at the outer rim because vibration is negligible at that point. It is to be understood that this configuration can be utilized with both backed and unbacked transducers, such as is known in the art.

Figure 10:
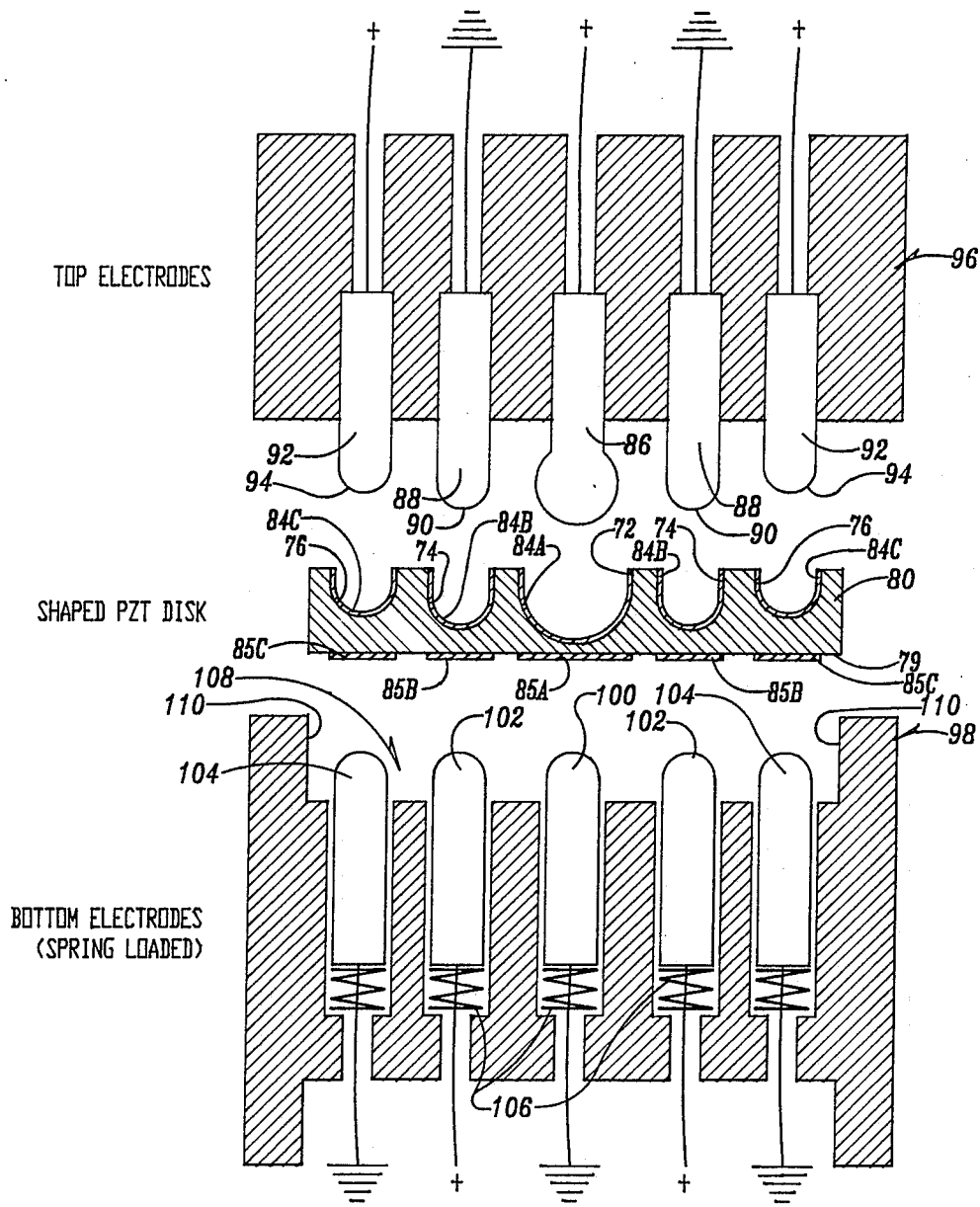
FIG. 10 is a sectional view of the components utilized to nonuniformly pole the piezoelectric piece of FIGS. 8 and 9.

The transducer probe of FIG. 10 can then be driven by a conventional piezoelectric transducer driver circuit (not shown). The beam profile of transducer probe 10 would be a Gaussian beam model for its center frequency. An example of a driver for producing ultrasonic Gaussian probe beam is a Panametrics pulser-receiver, available from Panametrics, Waltham, Mass. 02254, wherein the driving voltage is a negative spike pulse of minus 175 volts.

The general steps for producing a Gaussian piezoelectric transducer probe have therefore been described. The specifics of the production of a particular Gaussian probe are as follows.

For a Gaussian transducer with a center frequency of 2.25 megahertz (MHz), the ultimate thickness for disk 14 is calculated utilizing the follow equation:

$$f_o = v/2d$$

where v is the speed of longitudinal sound waves in the disk; d is thickness of the circular disk, and $f_0$ is the undamped thickness-mode fundamental frequency.

In this preferred embodiment, rod 28 is a piezoelectric material designated, such as is known in the art, as PZT-5A. Rod 28 is 0.75 inches (1.91 centimeters) in diameter. It is known that for PZT-5A material, v approximately equals 0.40 centimeters/microseconds (cm/μs). By utilizing the equation, the thickness ultimately for disk 14 should be approximately 0.035 inches (0.089 centimeters).

The size of piece 38 shown in FIG. 3 is also affected by how large hemispherical cavity 34 needs to be to achieve a required poling. The radius 48 of hemispherical cavity 34, and its relationship with regard to what will ultimately become disk 14 concerns the orientation and strength of the electrical field which will pass through piece 38. To insure that a sufficient electrical field is generated, tests were made utilizing a spherical electrode directly above a large flat conducting plate. By means well known within the art, the Z-component of the electrical field produced by a 0.5 inch (1.27 centimeter) diameter spherical electrode situated 0.48 inches (0.122 centimeters) above the conducting plate were compiled measuring the fields at three horizontal planes; namely at line 44, at line 36, and at the midpoint line 45 between lines 36 and 44. It was therefore determined that a sufficient electrical field would be generated to conform with a Gaussian function of desired characteristics through the ultimate disk 14 defined between lines 36 and 44.

Therefore, total thickness 58 of piece 38 as shown in FIG. 3 was 0.298 inches. This includes the 0.035 inch thickness for the ultimate disk 14 (measured between lines 36 and 44); the 0.25 inch radius 40 of hemispherical cavity 34; and allowing for a 0.013 inch distance between line 44 and the bottom of the hemispherical cavity 34 for the cut or kerf of a diamond wafer saw which is utilized to cut right above line 44.

The approximate electrical field needed for producing the Gaussian field is computed using methods given in D. R. Corson and P. Lorrain, *Introduction to Electromagnetic Field and Waves*, Chapter 4 (W. H. Freeman, San Francisco 1962).

The actual poling of piece 38, done with the basic configuration of FIG. 4, is performed in an immersion of diffusion pump oil, available from Dow-Corning under product designation 702, at a temperature of 95° plus or minus 2° centigrade. In the preferred embodiment, the applied high voltage DC power of 3700 volts produces a field of 75 volts/MIL (29.5 kV/cm) at the center of piece 38 at the midpoint between lines 44 and 36 (line 45). Maximum field is 80.8 volts/MIL at the center of piece 38 along line 44 and 73.2 volts/MIL at the center of the plane defined by line 36. In this preferred embodiment, the field is applied for four minutes and then removed. It is to be understood that the capacitance of piece 38 before and after poling are respectfully 1012 plus or minus 2 picofarads (pf) and 1193 plus or minus 2 pf, respectively, which represents an increase after poling of about 18%.

After poling, piece 38 is removed and cut into disk shape to produce a transducer element with a center frequency of about 2.25 MHz. In this preferred embodiment, if disk 14 is unbacked, it produces a quite narrow band ultrasonic pulse (Q=13).

It is to be understood that by altering the radius 40 of hemispherical cavity 34, the signal of the Gaussian transducer can be made larger so that field strength drops more slowly with radial distance from the center of the transducer. As has been shown, selection of a different type of piezoelectric material and using a different thickness can also effect properties of the transducer.

It is also to be understood that another important advantage of utilizing a Gaussian beam in both isotropic media and anisotropic media is that the ultrasonic beam can be described in one simple equation, as compared to the complex modeling needed for uniformly poled transducers. A discussion of these advantages can be found in R. B. Thompson and E. F. Lopes, J. Nondestr. Eval. 4, 107–123 (1984); and R. B. Thompson and B. P. Newberry, "A Model For The Propagation of Gausian Beams in Anisotropic Media", in *Review of Progress in Quantitative NDE*, Vol. 7, Edited by D. O. Thompson and D. E. Chimenti, (Plenum Press, New York, 1988), pp. 31–39. This allows information regarding the Gaussian beam to be programmed efficiently and easily into a computer for rapid generation of beam profiles.

Also, as previously stated, the Gaussian beam eliminates side lobes or diffraction of the beam to the point where spread of the beam width is quite small even at relatively low frequencies of 2.3 MHz in large propagation distances of 22 cm. This is very desirable in nondestructive evaluation.

By referring to FIGS. 5A and 5B, graphic displays of ultrasonic pulses generated with transducer probe 10 having a nonuniformly poled Gaussian response disk 14 are shown. FIG. 5A shows a time domain display of a narrow band pulse generated by an unbacked transducer probe 10 reflected from a planar target 10 cm away in water. The smooth shape of the pulse can be seen.

FIG. 5B shows a frequency domain display of the ultrasonic pulse, showing its center at approximately 2.3 MHz.

Figure 6A:
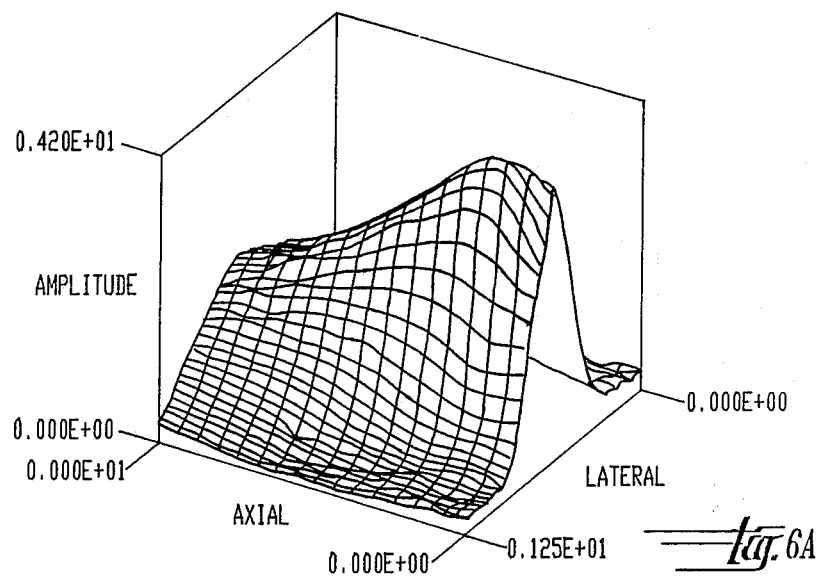
FIG. 6(a) is a three dimensional spatial mapping of the ultrasonic field response pattern of the piezoelectric transducer disk created by the steps of FIGS. 2–4.
Figure 6B:
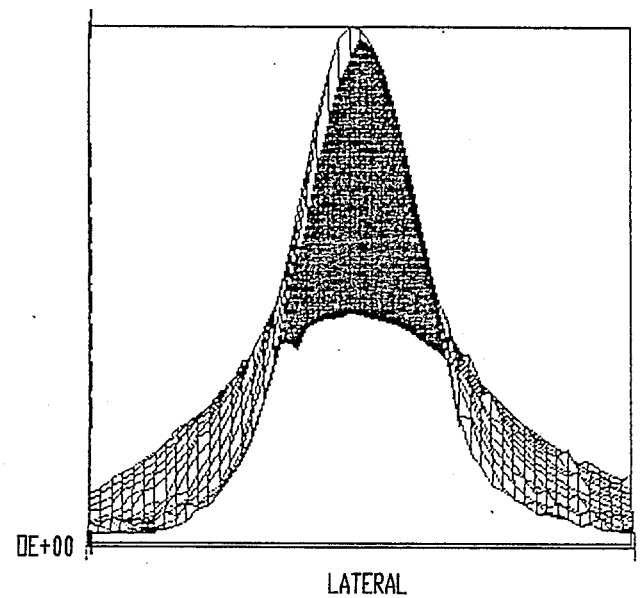
FIG. 6(b) is a front elevational view of FIG. 6(a).

FIGS. 6A and 6B show an actual three dimensional graphic display of the field profile of a nonuniformly poled Gaussian transducer probe 10 as measured by a scanning point probe. FIG. 6A shows in three dimensions the bell shaped and smooth nature of the pattern with no side lobes. This is furthermore shown in the front elevational view of FIG. 6B.

It can therefore be seen that the invention allows production of an advantageous nonuniformly poled Gaussian piezoelectric transducer according to the objects of the invention. Different types of response patterns can also be achieved with the invention. To exemplify this, a second preferred embodiment according to the invention will now be described with respect to FIGS. 7–11 A & B.

It has been found that an ultrasonic transducer having a beam pattern based on Bessel function profiles would be advantageous, especially for nondestructive evaluation. A Bessel profile probe can produce a beam that exhibits very little diffraction (beam spreading) in propagation. As can well be appreciated, a diffractionless, collimated intense ultrasonic beam has tremendous potential for practical applications in many fields.

Figure 7:
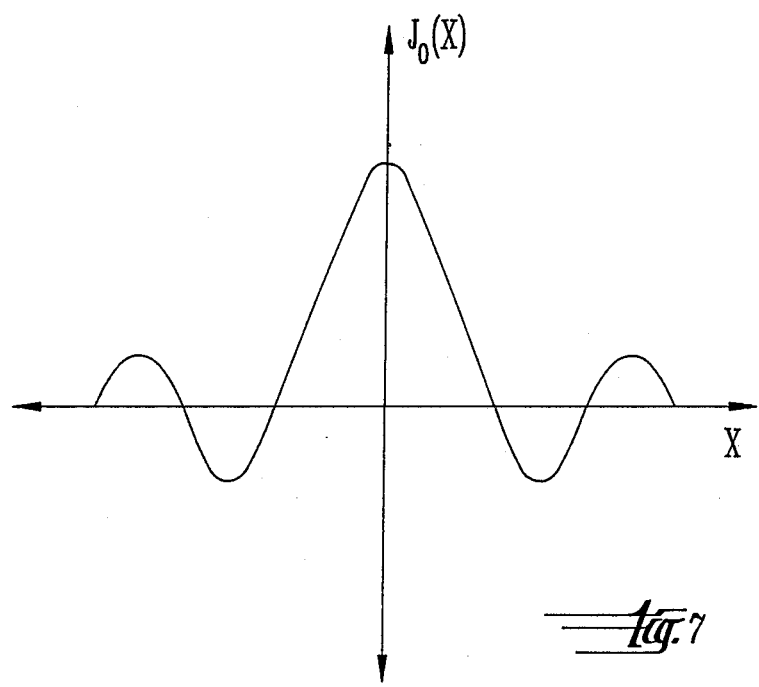
FIG. 7 is a graph of a Bessel function out to the third zero.

Although a Bessel function is much more complex than the simple bell-shaped profile of a Gaussian function, a piezoelectric transducer probe approximating a Bessel function can be achieved with the present invention. FIG. 7 depicts generally a truncated Bessel function. An actual Bessel function would consist of a large center lobe with an infinite number of side lobes, both positive and negative in nature. The nature of Bessel functions are well known within the art. It is noted that the primary characteristic of the Bessel function is the primary center lobe with the side lobes oscillating with each succeeding phase being opposite to the other. What this means when applied to a transducer disk is that certain portions of the transducer would undergo compression cycles while adjacent portions would undergo an expansion cycle.

The method of fabricating the transducer disk 14 to exhibit a Bessel function is quite similar to that described in preparing the Gaussian probe. By referring specifically to FIGS. 8–11 A&B, the description of the apparatus and method for producing the Bessel function will be set forth, particularly noting the differences from that in preparing a Gaussian function transducer probe.

Figure 8:
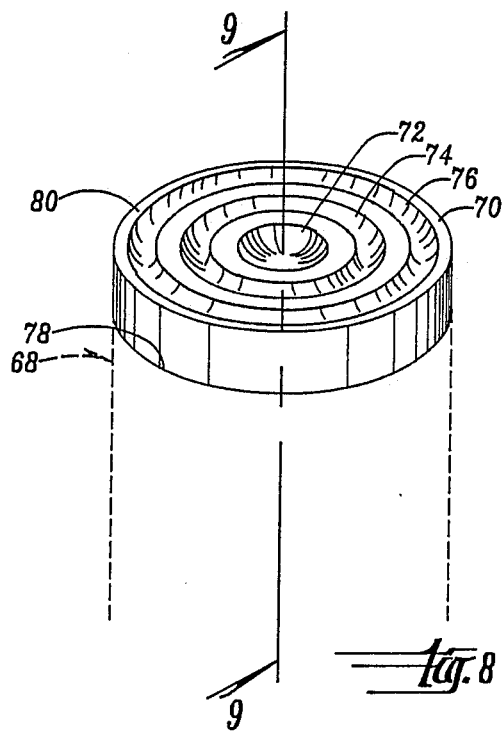
FIG. 8 is a perspective view of a piezoelectric rod with a hemispherical center cavity and two concentric hemispherical grooves machined in one end of the rod.

FIG. 8 shows a piezoelectric rod 68 similar to rod 28 in FIG. 2. Instead of simply one large hemispherical cavity in the center of end surface 70, a small hemispherical cavity 72 surrounded by first and second concentric curved-bottom grooves 74 and 76 are machined in end surface 70.

After these indentations are machined, which can again be done by a commercially available ball end cutter covered with surface abrasive particles on conventional machine shop equipment, rod 68 is cut along a plane defined by line 78 to define a bottom surface which is generally parallel to end surface 70.

Figure 9:
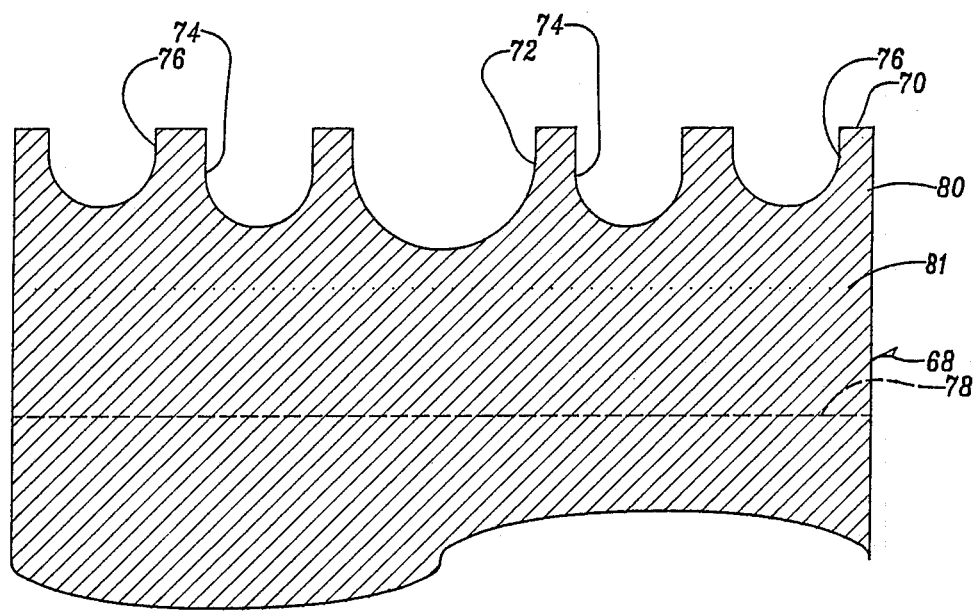
FIG. 9 is an enlarged sectional elevational view of the upper end of FIG. 8 taken along lines 9—9 of FIG. 8.

FIG. 9 shows in cross section piezoelectric piece 80 with cavity 72, and grooves 74 and 76. As can be seen, the depth and radius of cavity 72 is greater than the depth and radius of groove 74. The depth of groove 76 is less than the depth of groove 74, with the radius being roughly equal to groove 74. By comparing FIG. 9 with FIG. 7, it can be seen that the indentations in piece 80 approximate the Bessel function curve of FIG. 7, with grooves 74 and 76 representing the side lobes to the Bessel function.

Piece 80 is poled in a manner similar to that described with respect to the first embodiment for the Gaussian probe. The major differences are as follows.

In FIG. 10, it can be seen that a plurality of electrodes of varying polarities are utilized on opposite sides of piece 80. Piece 80 is first prepared for poling by having gold-over-chromium films 84a, 84b, and 84c evaporated into hemispherical cavity 72 and grooves 74 and 76 by means known within the art. Film 84 is shown in FIG. 10 and it is to be understood that there is no contact between the film 84a, 84b, and 84c in the indentations 72, 74, and 76, with each other so that electricity will not conduct between any of those indentations.

This same type of film is also deposited on the bottom of piece 80. It is to be understood, however, that it is deposited to mimic the indentations and film 84 in the indentations 72, 74, and 76 on top of piece 80. In other words, a circular section of film 85a of approximately the same diameter is deposited directly beneath hemispherical cavity 72. A spaced apart concentric ring of film 85b of approximately the same transverse width is deposited around that annular portion directly below groove 74. A separated and similar outer concentric ring of film 85c is deposited directly beneath groove 76.

There is no electrical interaction between these portions 85a, 85b, and 85c.

An array of top electrodes consists of a center ball electrode 86 which is adapted to mateably fit at least generally within hemispherical cavity 72. Electrode 86 is connected to the positive side of a high voltage DC power source. Electrodes 88, of generally cylindrical shape having rounded ends 90, are adapted to be mateably insertable into spaced apart locations in groove 74. Similarly, outer electrodes 92, being cylindrical with rounded ends 94, are mateably insertable into groove 76.

As can be seen in FIG. 10, outer electrodes 92 are also connected to the positive side of the electrical power source whereas electrodes 88 are connected to the negative or ground side of the power source.

Array 96 including electrodes 86, 88, and 92 can therefore be simultaneously mateably inserted into the top indentations 72, 74, and 76 of piece 80. Again, each electrode is electrically insulated and isolated from one another, as are the conductive coatings in cavity 72 and grooves 74 and 76.

A bottom array 98 of electrodes correspond with top electrode array 96. Bottom array 98, however, consists of a center electrode 100 of basically the same shape as electrodes 88 and 92; specifically without a ball end as compared to electrode 86. Electrodes 102 are spaced apart and electrically isolated from center electrode 100; whereas electrodes 104 are electrically isolated and spaced apart from electrodes 102.

Electrodes 100, 102 and 104 match up with the deposits of electrically conductive film 85a, 85b, and 85c on the bottom of piece 80. Electrode 100 is connected to the negative or ground side of the electrical power source; electrodes 102 are connected to the positive side; and electrodes 104 are also connected to the ground or negative side. It is to be noted that the electrodes in bottom array 98 are all spring loaded by springs 106. Additionally, a recess 108 is formed by sidewall 110 in bottom array 98 to mateably receive piece 80. Electrical contact between the electrodes of bottom array 98 and film 84 on the bottom of piece 80 is enhanced by the spring loaded electrodes. The top and bottom arrays 96 and 98 can then basically clamp the piece 80 within recess 108 during poling. Arrays 96 and 98, and the connections to the electrical power source, can again be adjusted and maintained in an insulated fixture such as a plexiglas cage (not shown).

After bringing the top and bottom electrode arrays 96 and 98 into mating abutment with piece 80, lowering the combination into an oil bath and heating the bath to a temperature of 95° plus or minus 2° C., high voltage DC power is supplied for a specified time period. Piece 80 is then withdrawn and allowed to cool to room temperature. Then, similar to the first described embodiment, the top indentations (cavity 72, grooves 74 and 76) are cut away by cutting a plane parallel to the bottom of piece 80 just below the bottom of hemispherical cavity 72 (see line 81 in FIG. 9). It is also to be understood that the film 85, deposited in different portions and rings on the bottom of piece 80 is removed, such as by sanding.

Therefore, a piezoelectric disk, such as disk 14 in FIG. 1, exists with nonuniform poling according to a Bessel function. The final steps would be to deposit, by processes known within the art, gold-over-chromium films to both sides of the disk and then install it into a case to produce a transducer probe such as transducer probe 10 in FIG. 1.

The specifics of a Bessel function probe according to this embodiment of the present invention, having a central frequency of 2.25 MHz, is as follows. The thickness of piece 80, cut from rod 68 (one inch diameter) was approximately 0.219 inches. The center hemispherical cavity 72 was 0.172 inches deep as its lowest point and 0.100 inches in radius. Groove 74 had a radius of 0.219 inches, a width of 0.125 inches and a maximum depth of 0.102 inches. Groove 76 has a radius of 0.38 inches, a width of 0.125 inches, and a maximum depth of 0.063 inches.

Similar to the first embodiment, the thickness of piece 80 was calibrated to allow for the kerf of a diamond wafer blade so that after removing the hemispherical cavity 72, and grooves 74 and 76, a 0.035 inch thick flat parallel faced disk, corresponding to the fundamental longitudinal mode at 2.25 MHz would exist. The radii of the hemispherical cavity and grooves 74 and 76 were chosen to correspond with the spacing of the Bessel function $J_0(x)$ shown in FIG. 7. The depths of these indentations 72, 74, and 76 were also chosen to produce electrical field intensities in accordance with the amplitude of the Bessel function. In this preferred embodiment, the electrical field at the first side lobe was 40% of that at the center, whereas the second (outer) lobe was 30% of that at the center. Cavity 72 and grooves 74 and 76 were machined to approximate those proportions.

It is also to be understood that in the preferred embodiment of FIGS. 7–11, each groove 74 and 76 would have three spaced apart electrodes 88 and 92; generally spaced apart equally around grooves 74 and 76. Correspondingly, three electrodes 102 and 104 would be spaced around the rings of film on the bottom of piece 80. Although FIG. 10 schematically depicts only two top and bottom electrodes per groove, it is to be understood that three is preferred, and more could be used if desired.

In this preferred embodiment, a voltage of 3,522 volts was applied across the electrodes for four minutes in the polarities shown in FIG. 10. The disk cut from piece 80 was then installed within a metal housing of a transducer probe without backing and driven by broad band voltage pulses.

Figure 11A:
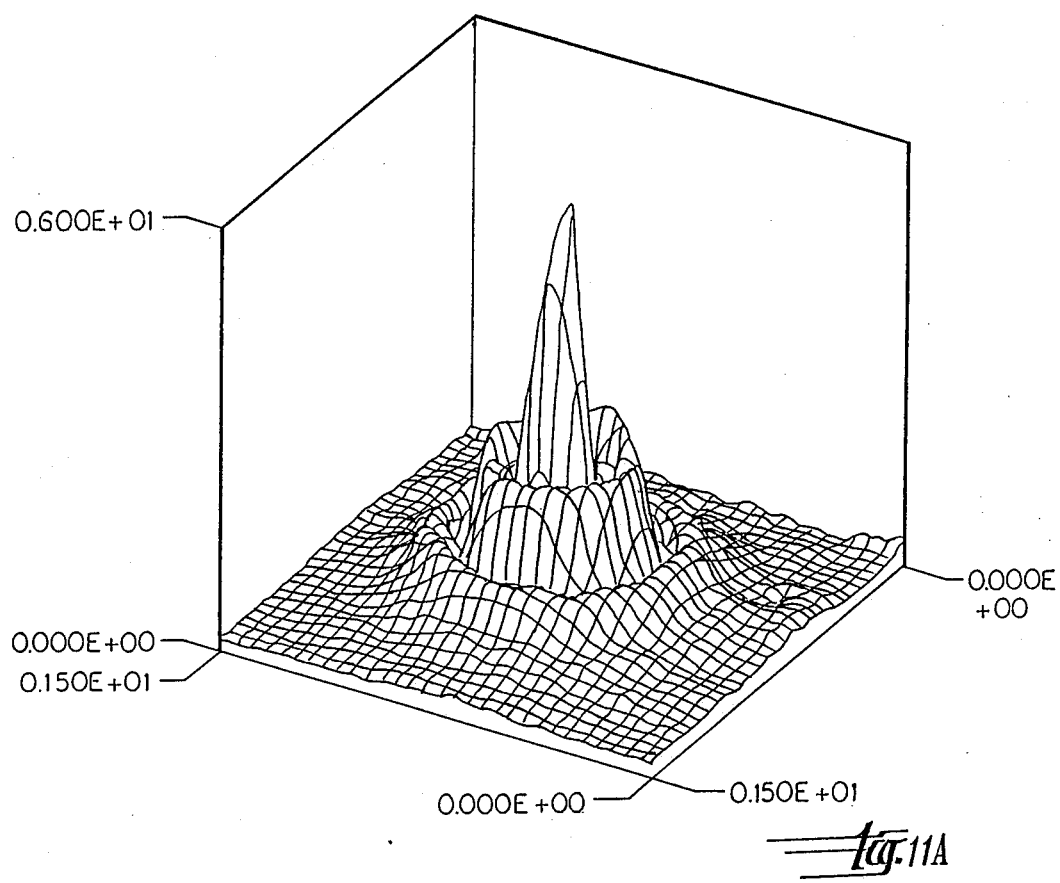
FIG. 11(a) is a three dimensional map of the ultrasonic field response pattern of the piezoelectric transducer disk created according to the steps of FIGS. 8–10.
Figure 11B:
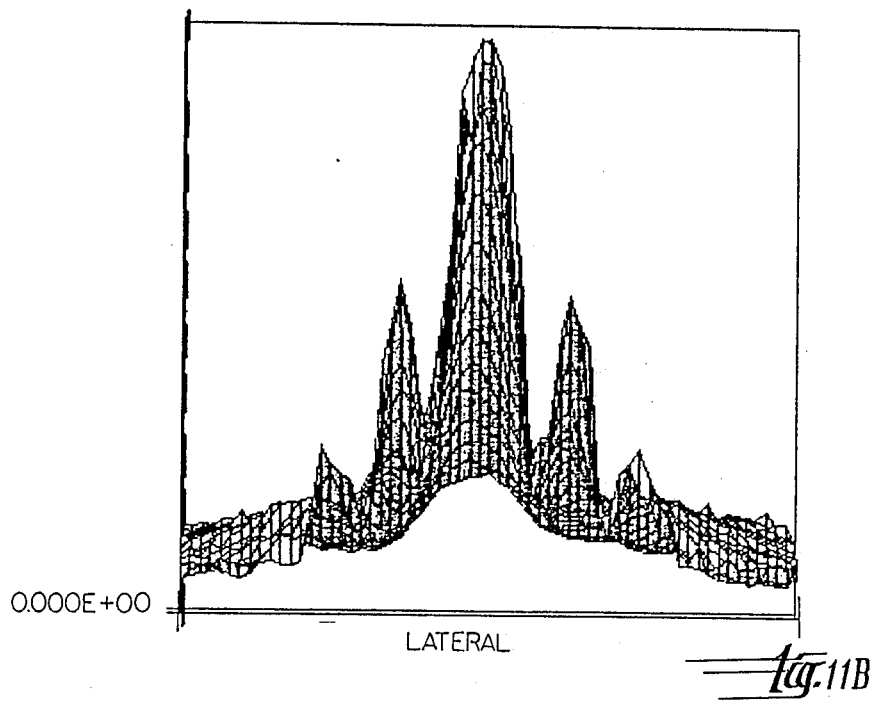
FIG. 11(b) is a front elevational sectional view of FIG. 11(a).

The Bessel function probe, when excited, causes the disk to vibrate in a manner where the center portion and outer portion vibrate out of phase with the middle concentric portion. The strength and spatial pattern of the ultrasonic field produced are graphically depicted at FIGS. 11A and 11B. As can be seen, FIG. 11A shows the amplitude (without respect to polarity) in three dimensions for the Bessel probe. FIG. 11A shows the field amplitude in a plane parallel to the transducer face and at a distance of 1.12" from it. A front elevational view, in section, of FIG. 11A is shown at FIG. 11B. A comparison of FIG. 11B with FIG. 7 shows the agreement of the transducer response with the Bessel function. FIG. 11B, like FIGS. 6A and 6B, was obtained by conducting a two dimensional scan in a plane perpendicular to the face of the transducer and containing the axis of the transducer disk. In these embodiments, a scan was made with the point probe to cover an actual distance of 0.125 inches to 9.125 inches and a lateral distance of plus or minus 0.775 inches. It is to be noted that in FIG. 11B, the strength of the first middle lobe was greater than what was called for in the Bessel model of FIG. 7. This strength could be reduced by reducing the depth of the first groove 76 in piece 80 which would reduce the strength of the poling field at that location.

It is further to be understood that amount of diffraction for these transducers depends upon frequency, the number of lobes, and the width of a lobe. In the preferred embodiment for the Bessel transducer with the fundamental frequency of 2.25 MHz, less diffraction exists when the transducer disk is excited to generate ultrasonic waves at its third harmonic frequency of approximately 7 MHz. It has further been found that, when the number of lobes is large, the range of a Bessel function transducer is directly proportionally to the frequency and number of lobes and also directly proportional to the square of the lobe width. The equation following describes this relationship:

$$R = (\text{constant}) (f) (n) (w^2)$$

Where f is the frequency, n is the number of lobes, and w is the width of the lobe.

By using this formula, large range (or low diffraction) can be achieved with a large Bessel transducer (large number of lobes and large lobe width). It can therefore be understood that by increasing the number of lobes and the size of the transducer, a decrease in diffraction can be achieved.

It will be appreciated that the present invention can take many forms and embodiments. The true essence and spirit of this invention are defined in the appended claims, and it is not intended that the embodiments of the invention presented herein should limit the scope thereof.

What is claimed is

1. A method for nonuniform poling of a piezoelectric transducer comprising:
    altering a flat first surface of a piezoelectric material to produce at least one indentation;
    cutting the piezoelectric material to present a opposite second surface generally parallel with the first surface;
    bonding a highly electrically conductive material to at least portions of the first and second surfaces;
    mateably inserting an electrode into each indentation;
    abutting an electrode of opposing polarity on the second surface opposite the first electrode;
    applying high voltage direct current electrical power through the electrodes and piezoelectric material for a predetermined duration;
    cutting the piezoelectric material to remove any indentations and to prepare a generally planar two-sided disk; and
    installing the disk within a transducer probe.

2. A method of claim 1 wherein the indentation is hemispherical.

3. The method of claim 2 wherein the electrode inserted in the indentation is spherical.

4. The method of claim 3 wherein the electrode of opposing polarity includes an indentation to mateably received a portion of the piezoelectric material including the second surface.

5. The method of claim 1 wherein the highly electrically conductive material is a metal film.

6. The method of claim 5 wherein the metal film is deposited onto the first and second surfaces.

7. The method of claim 6 wherein the metal film is comprised of a chromium base layer covered by a gold top layer.

8. The method of claim 1 wherein the first surface is altered to produce two or more indentations.

9. The method of claim 8 wherein conductive material is bonded only to the indentations on the first surface, and only to corresponding separated and electrically insulated positions on the second surface.

10. The method of claim 9 wherein the first and second sets of electrodes are positionable to the different portions of coatings on opposite surfaces, each directly opposite a pair of electrodes being of opposite polarity.

11. A method for producing a nonuniformly poled piezoelectric transducer element comprising:
    determining a desired beam response pattern for the element;
    quantifying the pattern by a mathematical function;
    sculpting a planar end of piezoelectric material in a manner correlated to the mathematical function;
    coding the sculpted surfaces on the planar end of the piezoelectric material;
    coding an opposite planar surface of the piezoelectric material on portions corresponding to sculpted portions on the planar end of the piezoelectric material;
    sandwiching the piezoelectric material between electrodes of preselected polarity;
    supplying electrical power to the electrodes for a preselected duration;
    removing the sculpted portions to leave a two sided planar piezoelectric element; and
    completely covering both sides of the planar element with a coating of conducting material.

12. The method of claim 11 wherein the mathematical function is a Gaussian function.

13. The method of claim 11 wherein the mathematical function is a Bessel function.

14. The method of claim 12 wherein the hemispherical centrally located cavity is sculpted in the planar end of the piezoelectric material.

15. The method of claim 14 wherein a spherical shaped electrode is mateably insertable into the hemispherical cavity.

16. The method of claim 12 wherein the electrode opposite the planar end includes a recessed cavity for mating insertion of the piezoelectric piece, including the opposite planar surface.

17. The method of claim 11 wherein the mathematical function is a Bessel function.

18. The method of claim 17 wherein a center hemispherical cavity and two concentric grooves are sculpted in the planar end of the piezoelectric material.

19. The method of claim 18 wherein the conductive coating on either planar surface is bonded to the surface in portions which are isolated and electrically insulated from one another.

20. The method of claim 19 wherein sets of electrodes are correlated with the coatings on opposite planar surfaces, each set of electrodes including at least one pair of electrodes of opposite polarity.

21. The method for nonuniform poling of piezoelectric transducers comprising:
    machining a hemispherical indentation into a planar end of a piezoelectric rod;
    cutting the end of the rod containing the hemispherical indentation in a plane parallel to the end surface at a distance spaced apart from the end surface to create a bottom surface;
    covering the hemispherical indentation and the bottom surface with conducting material;

positioning a generally mateably fitting ball-shaped electrode into the plated hemispherical indentation;

fitting the bottom of the piezoelectric material into a generally mating circular indentation in a second electrode;

positioning the piezoelectric material and first and second electrodes within a heated medium;

applying high voltage direct current electrical power of opposite polarity to the first and second electrodes for a predetermined duration;

removing the piezoelectric material and electrodes from the heated medium and removing the first and second electrodes;

removing the portion of the piezoelectric material containing the hemispherical indentation to produce a planar two sided disk, the disk containing nonuniform poling generally approximating a Gaussian function.

22. The method of claim 21 wherein the hemispherical indentation is of a depth related to the profile of an electrical field desired to be set up in the piezoelectric rod during poling.

23. The method of claim 21 wherein the step of cutting the end of the rod is preselected so that the distance between the plane parallel to the end surface is correlated to the center frequency of the transducer.

24. The method of claim 21 wherein the heated medium is oil means.

25. The method of claim 21 wherein the diameter of the hemispherical indentation is proportional to the electrical field strength through the piezoelectric material.

26. A method for nonuniform poling of a piezoelectric transducer comprising:

machining the top planar surface of a piezoelectric rod to produce a center hemispherical cavity and first and second concentric grooves surrounding the cavity;

depositing conducting material to the surfaces of the cavity and grooves;

cutting the metal rod in a spaced apart plane from the plane defining the end surface of the rod to produce a bottom surface;

depositing conducting material on the bottom surface in a pattern generally corresponding to the cavity and first and second grooves;

mateably inserting a ball shaped electrode into the center cavity;

mateably inserting one or more electrodes into each groove;

abutting an electrode to the conductive material on the bottom surface opposite the cavity;

abutting one or more electrodes to the highly conductive material on the bottom surface corresponding generally with the electrodes in the grooves;

applying high voltage direct current electrical power to the electrodes so that aligned and corresponding electrodes in the cavity and grooves as compared to on the bottom surface are of opposite polarities;

removing the electrodes; and cutting the piezoelectric material to remove the cavity and grooves to produce a planar two sided disk, the disk being nonuniformly poled.

27. The method of claim 26 wherein the spacing, depth, and diameter of the hemispherical cavity and first and second concentric grooves are proportional to the response pattern for the transducer.

28. The method of claim 27 wherein the response pattern generally approximates a Bessel function.

29. The method of claim 26 wherein the spacing, depth, and diameter of the central hemispherical cavity and first and second concentric grooves is proportional to the relationship between a center prominent lobe and first and second side lobes on each side of the center lobe according to a Bessel function.

30. The method of claim 26 wherein three electrodes are positionable at spaced apart positions around and in each groove.

31. The method of claim 30 wherein a plurality of electrodes are positionable at spaced apart positions corresponding to the electrodes for each groove.

32. The method of claim 31 wherein electrodes corresponding to the hemispherical cavity and second concentric groove are of like polarity, whereas electrodes corresponding to the first concentric groove is of opposite polarity.

33. The method of claim 26 comprising the first step of installing the planar two-sided disk within a transducer piston probe housing for connection to a transducer driving means.

* * * * *

UNITED STATES PATENT AND TRADEMARK OFFICE
CERTIFICATE OF CORRECTION

PATENT NO. : 4,961,252

DATED : October 9, 1990

INVENTOR(S) : Hsu, et al

It is certified that error appears in the above-identified patent and that said Letters Patent is hereby corrected as shown below:

Column 15, line 60, delete the word "received" and
　　change to --receive--.

Column 16, line 18 and 20, delete the words "coding"
　　and substitute --coating--.

Signed and Sealed this

Seventh Day of April, 1992

Attest:

HARRY F. MANBECK, JR.

Attesting Officer　　　Commissioner of Patents and Trademarks